United States Patent [19]

Shapiro

[11] Patent Number: 4,791,923
[45] Date of Patent: Dec. 20, 1988

[54] TRACHEAL TUBES

[75] Inventor: Seymour W. Shapiro, Lowell, Ind.

[73] Assignee: Bivona Surgical Instruments, Inc., Gary, Ind.

[21] Appl. No.: 941,574

[22] Filed: Dec. 11, 1986

Related U.S. Application Data

[63] Continuation of Ser. No. 850,428, Apr. 8, 1986, abandoned, which is a continuation of Ser. No. 582,064, Feb. 21, 1984, abandoned.

[51] Int. Cl.$^4$ ............................................. A61M 16/00
[52] U.S. Cl. ................................................. 125/207.15
[58] Field of Search ...................... 128/207.15; 604/99, 604/100, 101

[56] References Cited

U.S. PATENT DOCUMENTS

| | | | |
|---|---|---|---|
| 3,481,339 | 12/1969 | Millet Puig | 128/207.15 |
| 3,731,691 | 5/1973 | Chen | 604/100 |
| 4,020,849 | 5/1977 | Jackson | 604/99 |
| 4,119,101 | 10/1978 | Igich | 128/207.15 |

FOREIGN PATENT DOCUMENTS 693510  7/1953  United Kingdom ........... 128/207.15

Primary Examiner—Edward M. Coven
Assistant Examiner—J. P. Lacyk
Attorney, Agent, or Firm—Emrich & Dithmar

[57] ABSTRACT

The present invention includes a tracheal tube in which a cuff is mounted on an elongated tube. The cuff includes an inner inflatable balloon member and an outer inflatable balloon member. The inner inflatable member is disposed on the elongated tube in surrounding relationship and the outer inflatable member is disposed on the elongated tube and over the inner member in surrounding relationship. The inner balloon member is operatively connected to a source to receive gases for inflation to a diameter corresponding to the smallest diameter of the trachea. The outer balloon is operatively connected either to a positive ventilation device or to the airway pressure corresponding to the pressure in the respiratory tract to seal the respiratory tract during high pressure phases of mechanical ventilation.

8 Claims, 1 Drawing Sheet

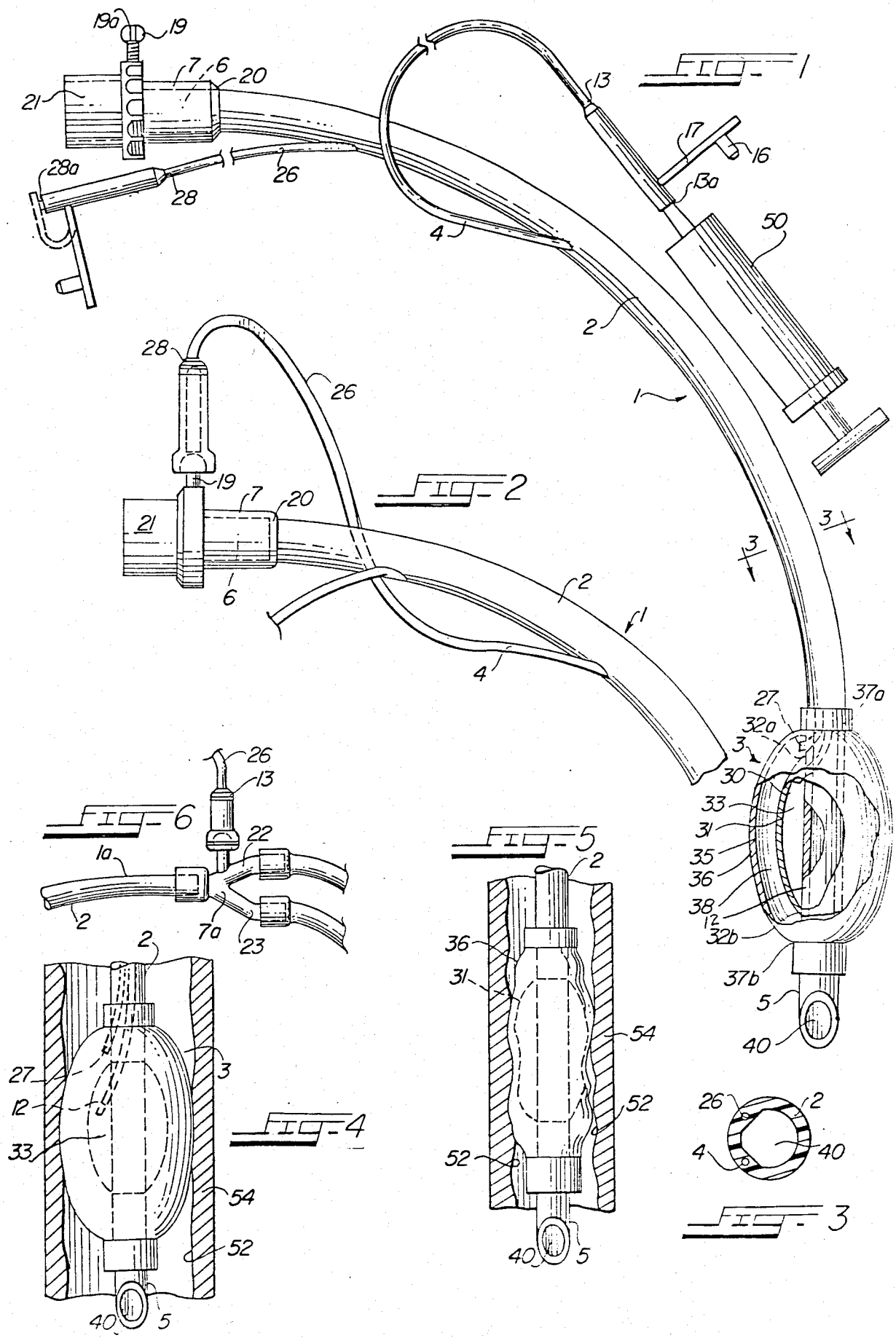

TRACHEAL TUBES

This is a continuation of application Ser. No. 850,428, filed Apr. 8, 1986 now abandoned, which in turn is a continuation of application Ser. No. 582,064, filed Feb. 21, 1984, now abandonded.

BACKGROUND OF THE INVENTION

The present invention relates to tracheal tubes and, more particularly, to tracheal tubes of the type embodying a cuff for effecting a seal between the tube and a trachea.

As is well known in the art, tracheal tubes are commonly inserted into a person's trachea for various purposes; for example, to enable the person to breathe, or to enable intermittent positive pressure ventilation of the respiratory tract to be carried out. The tracheal tube of the present invention is of the cuffed type and is particularly well adapted for the mechanical ventilation of the respiratory tract, especially where high ventilating pressures are utilized.

Tracheal tubes, as that term is used herein, may be of different types, such as, for example, orotracheal tubes, nasotracheal tubes and tracheostomy tubes. Typically, such tubes include a main body portion in the form of an elongated tube made of flexible material such as, rubber polyvinylchloride, or they may be stiff or rigid, made of material such as stainless steel.

There are two types of cuffed tracheal tubes commonly used in the art. One type of tracheal tube is characterized by a cuff including a cover filled with resilient material, with the cover normally being disposed in expanded position and being collapsed by applying a vacuum thereto during insertion or removal of the tube into or from the trachea. A tracheal tube of this general type is described in U.S. Pat. No. 3,640,282, issued to Kamen and Wilkinson on Aug. 6, 1970, and forms the subject matter for my co-pending application Ser. No. 291,322, entitled Tracheal Tube and filed Aug. 10, 1981.

A second type of tracheal tube is characterized by a cuff which is not filled with a resilient material. Such cuffs are uninflated or deflated in condition. With such devices, after the intubation device has been inserted into the trachea, the cuff is inflated like a balloon, by feeding air or other working fluid thereinto at a positive pressure to thereby expand the cuff into engagement with the inner wall of the trachea. However, it has been found that such devices have several inherent disadvantages, the primary disadvantage being that they commonly cause injury to the trachea, causing lesions such as tracheal stenosis, tracheal malacia and localized erosion, particularly if it is necessary for the tube to remain in the trachea for prolonged periods of time.

Current techniques of mechanical ventilation of the respiratory tract often employ relatively high positive air pressure. This pressure is highest at the peak of the inspiratory phase and lowest at the termination of the expiratory phase. The human trachea is elastic and stretches increasing in diameter, in part, with increasing pressure in the respiratory tract. The degree of elasticity of the trachea varies and is dependent upon a number of factors, the majority of which cannot be controlled during mechanical ventilation.

Mechanical ventilation techniques and tracheal elasticity create a problem for cuffed endotracheal tubes to overcome. If the cuff is of the air-filled type, the volume of air required to prevent leakage of ventilation gases at peak inspiratory airway pressure exceeds the volume of air needed in the cuff during expiration. The cuff must be overinflated during expiration to prevent leakage during inspiration. The result in many instances is a progressive stretching of the trachea with ultimate tracheal injury.

On the other hand, when the cuff on the tracheal tube is of the expandable-material filled type, such as, for example, the type disclosed in the aforementioned Kamen and Wilkinson U.S. Pat. No. 3,640,282, the cuff contents exert progressively less force against the tracheal wall as the elastic trachea's volume is expanded at peak inspiratory pressure. If this expansion of the elastic trachea is of sufficient magnitude, the result is an inadequate seal between the cuff and the trachea.

Heretofore, in an attempt to insure the proper seal between the trachea and a cuffed tracheal tube during mechanical ventilation and to minimize or prevent tracheal injury, cuff inflator machines have been used. These machines either attempt to vary the cuff volume and pressure synchronously with a companion ventilating machine or to maintain a constant cuff pressure while varying the cuff volume during the changing requirements of a complete inspiration/expiration cycle. These machines have several disadvantages, among which are that they are expensive and are subject to the maintenance and calibration problems inherent to precise machinery.

SUMMARY OF THE INVENTION

The present invention provides a novel tracheal tube which is particularly useful during high positive pressure ventilation of a respiratory tract. The present invention provides an effective seal between the tracheal tube and the trachea, without the peak pressure in the cuff exceeding the peak pressure of the airway passage. The controlled pressure in the cuff provides a tracheal tube which is more comfortable and minimizes injuries to the trachea.

Briefly, the present invention includes a tracheal tube in which a cuff is mounted on an elongated tube. The cuff includes an inner inflatable balloon or member and an outer inflatable balloon or member. The inner inflatable balloon or member is disposed on the elongated tube in surrounding relationship. The outer inflatable member is disposed on the elongated tube and over the inner member also in surrounding relationship. A second tube has a distal end in communication with the inner inflatable member and is adapted to receive gases at the proximal end for inflating the inner balloon member to a diameter corresponding to the smallest diameter of the trachea, normally at the lowest positive ventilation pressure. A third tube has a distal end in communication with the outer inflatable member and a proximal end adapted to be received in communication with the interior of the first elongated tube for allowing the gases of positive ventilation to pressurize the third elongated tube and the outer inflatable member to a pressure corresponding to the pressure in the respiratory tract to seal the respiratory tract during high pressure phases of respiration.

Thus, the present invention provides an apparatus and method which prevents the peak pressure in the cuff from exceeding peak airway pressures and is practical, simple, and efficient in operation and can be readily and economically practiced. Other features and advantages of the present invention will be apparent from the following description and claims and are illustrated in the accompanying drawings which, by way of illustration, show a preferred embodiment of the present invention and the principles thereof in what is now considered to be the best mode in which to apply these principles. Other embodiments of the invention employing the same or equivalent principles may be used and structural changes may be made as desired by those skilled in the art without departing from the present invention and the purview of the appended claims.

DESCRIPTION OF THE DRAWINGS

FIG. 1 is a side elevational view of a tracheal tube embodying the principles of the present invention;

FIG. 2 is a fragmentary, side elevational view of a portion of the tracheal tube shown in FIG. 1, showing parts thereof disposed in a different operative position;

FIG. 3 is a cross-sectional view of the tracheal tube shown in FIG. 1, looking in the direction of the arrows 3—3 in FIG. 1;

FIG. 4 is a fragmentary elevational view of the of the tracheal tube shown in FIG. 1, showing the cuff disposed in a trachea in an expanded position, the trachea being shown diagrammatically;

FIG. 5 is a view similar to FIG. 4 showing the cuff in substantially uninflated or deflated condition; and, FIG. 6 is a fragmentary view of a tracheal tube of the type shown in FIG. 1, illustrating a modified form of the present invention.

DETAILED DESCRIPTION

A tracheal tube or intubation device, generally designated by numeral 1, embodying the principles of the present invention, is shown in the drawings to illustrate what is now considered the best mode or preferred embodiment. Referring specifically to FIG. 1, the tracheal tube 1, includes the following major elements: an elongated tube 2, and a cuff 3 having an inner inflatable balloon or member 30 and an outer inflatable balloon or member 35.

The elongated tube 2 defines a passage 40 along its length for the purpose of feeding air, or the like, into and out of respiratory tract of a patient into whose trachea the tracheal tube 1 has been inserted. When the tracheal tube 1 is to be used as an endotracheal tube, such as either an orotracheal or nasotracheal tube, the elongated tube 2 is preferably expandable and may be made of any suitable material such as rubber, polyvinylchloride, or the like. However, in other instances, such as when the tracheal tube 1 is to be used as a tracheostomy tube, it may be desired to have the elongated tube 2 be rigid in construction and made of a suitable material such as stainless steel.

The elongated tube 2 has a distal end 5 for insertion into the trachea, and a proximal end 6 on which a connector 7 is mounted for connecting the elongated tube 2 to suitable sources of gases for respiration or anesthesia, or to a ventilating machine. It will be understood by those skilled in the art that the elongated tube 2 may be of any suitable length, such tubes commonly being in the nature of 9-14 inches in length, when used as an endotracheal tube, and commonly being considerably shorter when used as a tracheostomy tube.

Cuff 3 will normally be disposed closer to the distal end 5 of the elongated tube 2 than to the proximal end 6. Normally, cuff 3 is spaced from the distal end portion 5 a distance in the range of approximately one-half to three-fourths of an inch on an elongated tube 2 having an overall length of fourteen inches. However, as will be appreciated by those skilled in the art, the cuff 3 may be disposed at any suitable location along the elongated tube 2, the particular location thereof depending upon the intended use of the intubation device 1. For example, the above range would be appropriate if the elongated tube 2 is to be inserted into the windpipe or trachea only. However, if the intubation device 1 is to be inserted further into the trachea, such as for example, into the bronchi, the cuff 3 preferably would be spaced a greater distance from the distal end 5 so that it would remain in the trachea when the distal end 5 is inserted into the bronchi.

Cuff 3, encircling a portion of the outer surface of the elongated tube 2, includes an inner inflatable balloon or member 30 and an outer inflatable balloon or member 35. The inner inflatable balloon or member 30 includes an expandable cylindrical covering 31 disposed on the elongated tube 2 in surrounding relationship. The edge surfaces 32a and 32b of the cylindrical covering 31 are secured to the outer surfaces of the elongated tube 2 in a substantially airtight manner to define an inner chamber 33, as shown in FIG. 1.

The outer inflatable balloon or member 35 includes an expandable cylindrical covering 36 disposed on the elongated tube 2 over the inner member 30 in surrounding relationship. The edge surfaces 37a and 37b of the expandable cylindrical covering 36 are secured to the outer surfaces of the elongated tube 2 in a substantially airtight manner to define an outer chamber 38.

The expandable cylindrical coverings 31 and 36 of the inner and outer members 30 and 35, respectively, may be made of any suitable material such as latex rubber or a suitable plastic sheet material, such as polyvinylchloride.

Means for inflating the inner member 30 include an inner inflation tube 4 having a distal end portion 12 and a proximal end portion 13. Inner inflation tube 4 extends into the inner chamber 33, the space between the cylindrical covering 31 of inner member 30 and the elongated tube 2, at its distal end portion 12, as shown in FIGS. 1 and 4.

Means for inflating the outer member 35 include an outer inflation tube 26 having a distal end portion 27 and a proximal end portion 28. Outer inflation tube 26 extends into the outer chamber 38, the space between the cylindrical covering 36 of the outer member 35 and the cylindrical covering 31 of the inner member 30, at its distal end portion 27, as shown in FIGS. 1 and 4.

Portions of the inner and outer inflation tubes 4 and 26 can be formed integrally with the elongated tube 2 with proximal end portions 13 and 28 projecting outwardly from the proximal end 6 of elongated tube 2, as can best be seen in FIGS. 1 and 3. However, as will be appreciated by those skilled in the art, either or both of the inner or outer inflation tubes 4 and 26 may be formed separately from the elongated tube 2, inserted and sealably affixed into the respective inner and outer chambers 33 and 38 in a suitable manner without departing from the broader aspects of the present invention.

Inner inflation tube 4 is shown connected at its proximal end 13 to a pump 50 suitable for inflating inner member 30 with air. After the inner member 30 has been inflated, the proximal portion 13 of inner inflation tube 4 is pinched to close the passage within tube 4 and to allow the removal of pump 50 without loss of air. A stopper 16 is affixed to the proximal end portion 13 by means of an expandable strap 17. Stopper 16 can be fitted into the opening 13a of the inner inflation tube 4 to secure the inflation of inner member 30 in a semi-permanent manner. In use, the inner balloon member 30 is inflated by pump 50 to seal against the walls 52 of the trachea 54, when the trachea is at its smallest volume, the position as shown in FIG. 5. This provides a minimum volume seal of the trachea.

The outer inflation tube 26 may be used to inflate outer member 35. Outer inflation tube 26 is also equipped with a stopper 16 affixed to an expandable strap 17 which can be manually bent over to fit the stopper 16 into the opening 28a of outer inflation tube 26 to maintain a positive pressure within the interior of outer balloon member 35.

However, when used with mechanical ventilation of the respiratory tract, it is preferred that the pressure within the outer member 35 fluctuates with the pressure of the respiratory tract or airway pressure within airway passage 40. Thus, an embodiment of the present invention includes an outer member 35 in communication with the interior or airway passage 40 of the elongated tube 2 for subjecting the outer chamber 38 of the outer inflatable balloon member 35 to substantially the same pressure as the interior of the elongated tube and, consequently, to the pressure of the airway passage 40 or respiratory tract. Referring now to FIG. 2, connector 7 has one end portion 20 connected to the proximal end portion 6 of the elongated tube 2 and another end portion 21 projecting outwardly therefrom for connection to sources of respiration gases, anesthesia and the like or to a mechanical ventilation machine. A coupling 19 is embodied in the connector 7 as an integral part thereof projecting laterally outward from the body of the connector 7 and adapted to receive the proximal end portion 28 of the outer inflation tube 26. Coupling 19 includes a passageway 19a in communication with the interior of the connector 7 and the airway passage 40 of the elongated tube 2.

As will be appreciated by those skilled in the art, the coupling 19 is shown herein as part of the connector 7 merely by way of illustrating one of the preferred forms of the present invention and not by way of limitation, the coupling 19 may be connected to the elongated tube 2 in other ways, such as directly to the elongated tube 2 as an integral part thereof.

Another embodiment is illustrated in FIG. 6, wherein identical parts which are the same as are those shown in FIGS. 1-5 are indicated by the same reference numerals, and parts which are similar to but have been substituted for parts shown in FIGS. 1-5 are shown by the same reference numerals with the suffix a added. Tracheal tube 1a shown in FIG. 6 is of the same construction as the tracheal tube 1 shown in FIGS. 1-5 except that a modified form of connector 7a has been substituted for the connector 7. Connector 7a has an end portion 20 in communication with the proximal end portion 6 of the elongated tube 2. The end portion 21a of the connector 7a is not of a one piece construction but embodies two branches 22 and 23 by which the tracheal tube 1a may be connected to two separate lines or hoses for connecting the patient to a source of respiratory gases such as oxygen or general anesthetic or the like.

Normally, during mechanical ventilation, gases having a relative humidity of one hundred percent are delivered to the lungs. In most instances, moisture in the cuff 3 is undesirable in that it condenses and forms an uncomfortable weight in the trachea and distorts the shape of the cuff. To protect against this, if desired, a moisture absorbing cartridge, not shown, may be interposed between the coupling 19 and proximal end of the portion 13 of outer inflation tube 38. This cartridge may be of any suitable type readily available on the market, but preferable should be of the type that changes color when it becomes moisture laden so as to alert those in attendance that a replacement cartridge is needed.

In operation, the tracheal tube is inserted into the trachea of a patient with the inner and outer balloon members 30 and 35 deflated and presenting a compact streamlined profile. After the tracheal tube 1 is in place, pump 50 attached to inner inflation tube 4 inflates inner member 30 to seal the trachea while the trachea is in its smallest diameter, generally corresponding to low ventilation pressures, as shown in FIG. 5. The proximal end portion 13 of tube 4 is pinched, blocking the passage of gas from the inner member 30 while stopper 16 is pressed firmly within the opening of the proximal end portion 13 of the inner inflation tube 4. Thus, the inner balloon serves to prevent aspiration when the airway pressure is low and trachea 54 is at its smallest volume or diameter.

End portion 21 of connector 7 is coupled in communication to a mechanical ventilation machine (not shown). Air being forced through the elongated tube 2 inflates the respiratory tract and causes the trachea to expand elastically. Outer inflation tube 26 is connected in communication with elongated tube 2 by connecting proximal end portion 28 of the outer inflation tube 26 to coupling 19 of connector 7. Positive pressure in the elongated tube 2 forces the inflation of the outer member 35 at a pressure corresponding to the pressure exerted upon the respiratory tract and the trachea, as shown in FIG. 4. Therefore, outer member 35 expands to seal the trachea at a pressure corresponding to the overall pressure in the respiratory tract, and contracts as the pressure falls.

Thus, while the preferred embodiments of the present invention have been illustrated and described, it is to be understood that these are capable of variation and modification, and the present invention should not be limited to the precise details set forth but should include such changes and alterations as fall within the purview of the following claims.

I claim:

1. A tracheal tube for insertion into the trachea of a patient for enabling positive pressure ventilation of the respiratory tract to be carried out said tracheal tube comprising:
    an elongated tube having an outer surface, a proximal end portion and a distal end portion, the interior of said tube defining an airway between its end portions;
    a cuff mounted on said outer surface of said elongated tube near its distal end portion, said cuff including an inner inflatable member and an outer inflatable member, said inner inflatable member affixed to and encircling a portion of said elongated tube, and said outer inflatable member positioned over said inner inflatable member in surrounding relationship and affixed to and encircling a portion of said elongated tube;
    inner member inflation means including an inner inflation tube having a proximal end and distal end, said inner inflation tube having its proximal end connectable to a source of positive pressure and its distal end communicating with the interior of said inner member for communicating the interior of said inner member with the source of positive pressure for creating a constant positive pressure within said inner member for semi-permenantly inflating said inner member within said outer member thereby extending said outer member into sealing engagement with the walls of a trachea when the trachea is at its smallest diameter;

outer member inflation means including an outer inflation tube having a proximal end and a distal end, said outer inflation tube having its distal end communicating with the interior of said outer member; and connecting means on said elongated tube near its proximal end, said connecting means being constructed and arranged to communicate the interior of said elongated tube with at least one source of gas for positive pressure ventilation of the respiratory tract, and said connecting means defining coupling means for receiving the proximal end of said outer inflation tube in communication with the interior of the elongated tube whereby the interior of said outer member is communicated through said outer inflation tube with the interior of said elongated tube for inflating and deflating the outer inflatable member relative to its extended condition in accordance with the increasing and decreasing airway pressure in the interior of said elongated tube to permit adjustment of said outer inflatable member to the trachea's diameter when said diameter is greater than its smallest diameter.

2. A tracheal tube as defined in claim 1 in which said inner inflatable member includes an expandable cylindrical covering having edge surfaces, said expandable cylindrical covering encircling a portion of said elongated tube, said edge surfaces of said cylindrical covering secured to the outer surface of said elongated tube in a substantially air tight manner to define an inner chamber.

3. A tracheal tube as defined in claim 1 in which said outer inflatable member includes an expandable cylindrical covering having edge surfaces, said expandable cylindrical covering encircling a portion of said elongated tube and extending over said inner inflatable member in surrounding relationship, said edge surfaces secured to the outer surface of said elongated tube in a substantially air tight manner to define an outer chamber.

4. The tracheal tube as defined in claim 1 wherein said connecting means comprise a connector affixed in communication with the proximal portion of said elongated tube, said connector having a coupling in communication with the interior of said elongated tube, said coupling adapted to communicate with and receive said proximal end portion of said outer inflation tube.

5. A tracheal tube as defined in claim 1, wherein said inner inflation tube includes connecting means at its proximal end portion having a coupling portion for connecting said inner inflation tube to a source of positive pressure for establishing the constant positive pressure within said inner member and a closing portion cooperating with said coupling portion for maintaining the constant positive pressure within said inner member.

6. A tracheal tube as defined in claim 1, wherein said outer inflation tube defines coupling means at its proximal end portion constructed and arranged for connecting said outer inflation tube to said connecting means of said elongated tube in communication with the interior of said elongated tube.

7. A tracheal tube for insertion into the trachea of a patient for enabling positive pressure ventilation of the respiratory tract to be carried out said tracheal tube comprising:

an elongated tube having an outer surface, a proximal end portion and a distal end portion, the interior of said tube defining an airway between its end portions;

a cuff mounted on said outer surface of said elongated tube near its distal end portion, said cuff including an inner inflatable member and an outer inflatable member, said inner inflatable member including an inner expandable cylindrical covering having edge surfaces, said inner covering encircling a portion of said elongated tube, said edge surfaces of said inner covering being secured to the outer surface of said elongated tube in a substantially air tight manner to define an inner chamber, said outer inflatable member including an outer expandable cylindrical covering having edge surfaces, said outer covering encircling a portion of said elongated tube and extending over said inner covering in surrounding relationship, said edge surfaces of said outer covering being secured to the outer surface said elongated tube in a substantially airtight manner to define an outer chamber;

inner member inflation means including an inner inflation tube having a proximal end and a distal end, said inner inflation tube having its proximal end connectable to a source of positive pressure and its distal end communicating with the inner chamber of said inner member for communicating the interior of said inner member with the source of positive pressure for creating a constant positive pressure within said inner member for semi-permanently inflating said inner member within said outer member thereby extending said outer member into sealing engagement with the walls of a trachea when the trachea is at its smallest diameter;

outer member inflation means including an outer inflation tube having a proximal end and a distal end, said outer inflation tube having its distal end communicating with the outer chamber of said tube outer member; and connecting means on said elongated tube near its proximal end, said connecting means being constructed and arranged to communicate the interior of said elongated tube with at least one source of gas for positive pressure ventilation of the respiratory tract, and said connecting means defining coupling means for receiving the proximal end of said outer inflation tube in communication with the interior of the elongated tube whereby the outer chamber of said outer member is communicated through said outer inflation tube with the interior of said elongated tube for inflating and deflating the outer inflatable member relative to its extended condition in accordance with the increasing and decreasing airway pressure in the interior of said elongated tube to permit adjustment of said outer inflatable member to the trachea's diameter when said diameter is greater than its smallest diameter.

8. The tracheal tube as defined in claim 7 wherein said connecting means comprise a connector affixed in communication with the proximal portion of said elongated tube, said connector having a coupling in communication with the interior of said elongated tube, said coupling adapted to communicate with and receive said proximal end portion of said outer inflation tube.

* * * * *